(12) United States Patent
Halbach

(10) Patent No.: US 11,246,989 B1
(45) Date of Patent: Feb. 15, 2022

(54) SMALL SYRINGE WITH ENHANCED READABILITY

(71) Applicant: Nicholas William Halbach, Hayward, CA (US)

(72) Inventor: Nicholas William Halbach, Hayward, CA (US)

(*) Notice: Subject to any disclaimer, the term of this patent is extended or adjusted under 35 U.S.C. 154(b) by 0 days.

(21) Appl. No.: 15/865,283

(22) Filed: Jan. 9, 2018

Related U.S. Application Data

(60) Provisional application No. 62/708,564, filed on Dec. 12, 2017, provisional application No. 62/707,919, filed on Nov. 24, 2017, provisional application No. 62/602,138, filed on Apr. 12, 2017, provisional application No. 62/601,904, filed on Apr. 4, 2017, provisional application No. 62/601,917, filed on Apr. 4, 2017, provisional application No. 62/601,840, filed on Apr. 3, 2017, provisional application No. 62/499,872, filed on Feb. 6, 2017, provisional application No. 62/499,873, filed on Feb. 6, 2017, provisional application No. 62/499,862, filed on Feb. 6, 2017, provisional application No. 62/499,704, filed on Feb. 6, 2017, provisional application No. 62/498,975, filed on Jan. 10, 2017.

(51) Int. Cl.
A61M 5/31 (2006.01)

(52) U.S. Cl.
CPC ... *A61M 5/3129* (2013.01); *A61M 2005/3126* (2013.01); *A61M 2205/70* (2013.01)

(58) Field of Classification Search
CPC .............. A61M 5/3129; A61M 5/3137; A61M 2005/3126; A61M 2005/314; A61M 2205/58; A61M 2205/583; A61M 2205/584; A61M 2205/585; A61M 2205/586; A61M 5/178; A61M 5/28; A61M 5/281; A61M 5/31; A61M 5/3134; A61M 5/3135; A61M 2005/3125; A61M 2205/00; A61M 2205/19; A61M 2205/581; A61M 2205/582; A61M 2205/59; A61M 2240/00; A61M 2250/00
See application file for complete search history.

(56) References Cited

U.S. PATENT DOCUMENTS 2,586,581 A 2/1952 Tschischeck
3,885,562 A * 5/1975 Lampkin ............ A61M 5/3129
 604/189
4,018,223 A 4/1977 Ethington
(Continued)

FOREIGN PATENT DOCUMENTS

DE 4323466 A1 1/1994
EP 0084583 A1 8/1983
(Continued)

OTHER PUBLICATIONS

English Translation of FR2693909A1. (Year: 1994).*

Primary Examiner — Kami A Bosworth
(74) Attorney, Agent, or Firm — David Pressman

(57) ABSTRACT

A modified syringe barrel as a component for a syringe assembly. The barrel's outer wall bears a longitudinally-aligned projection which extends laterally and outwardly away from the barrel, thereby providing added surface for syringe indicia presentation, including elements of a graduated scale. The effect is a more flattened view of syringe markings for significant improvement in readability.

1 Claim, 7 Drawing Sheets

(56) References Cited

U.S. PATENT DOCUMENTS

| | | | |
|---|---|---|---|
| 4,178,071 A | 12/1979 | Asbell | |
| 4,516,969 A * | 5/1985 | Kintner | A61M 3/00 604/187 |
| 4,743,234 A | 10/1988 | Leopoldi | |
| 5,062,828 A | 11/1991 | Waltz | |
| 5,242,405 A * | 9/1993 | Howe | A61M 5/3129 604/125 |
| 6,120,481 A | 9/2000 | Rennert | |
| 6,936,034 B2 | 8/2005 | Watkins | |
| 8,636,702 B2 | 1/2014 | Schiller | |
| 8,808,252 B1 * | 8/2014 | Fox | A61M 5/31511 604/218 |
| 9,192,723 B2 | 11/2015 | Creaturo | |
| 9,775,950 B2 | 10/2017 | Creaturo | |
| D914,872 S * | 3/2021 | Shaw | A61M 5/3129 D24/130 |
| 2009/0216198 A1 * | 8/2009 | Salas | A61M 5/3129 604/187 |
| 2013/0006188 A1 * | 1/2013 | Pommereau | A61M 5/178 604/189 |
| 2013/0072878 A1 * | 3/2013 | Avery | A61J 1/10 604/189 |
| 2015/0025472 A1 * | 1/2015 | Colwell | A61M 5/3129 604/189 |
| 2015/0073354 A1 | 3/2015 | Creaturo | |
| 2015/0231335 A1 | 8/2015 | Creaturo | |
| 2015/0306318 A1 | 10/2015 | Lockhart | |
| 2019/0298928 A1 * | 10/2019 | Shaw | A61M 5/3129 |
| 2020/0289761 A1 * | 9/2020 | Grigoreas | A61M 5/3156 |

FOREIGN PATENT DOCUMENTS

| | | | | |
|---|---|---|---|---|
| FR | 2693909 A1 * | 1/1994 | | A61M 5/3129 |
| FR | 2693909 A1 | 1/1994 | | |
| WO | WO2016176523 | 11/2016 | | |

* cited by examiner

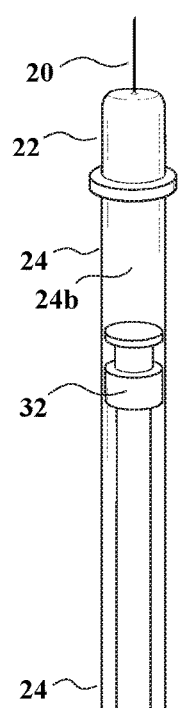 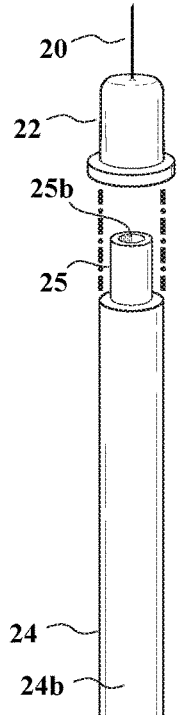 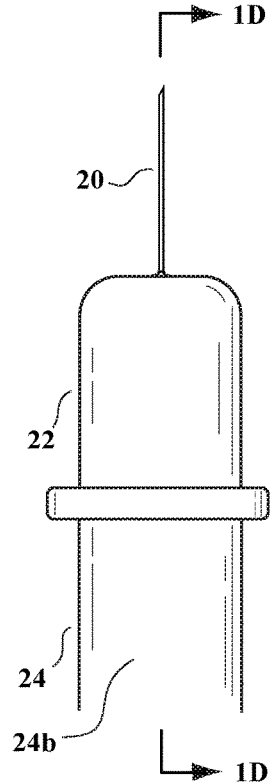 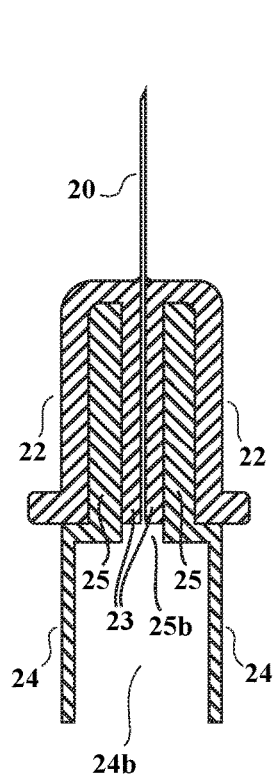
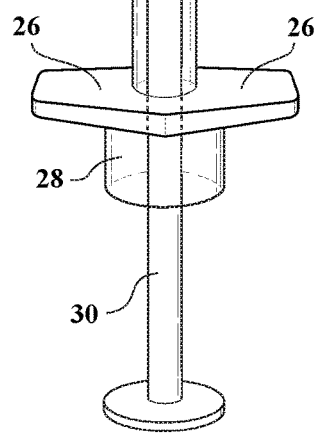
FIG. 1A
(PRIOR ART)
FIG. 1B
(PRIOR ART)
FIG. 1C
(PRIOR ART)
FIG. 1D
(PRIOR ART)

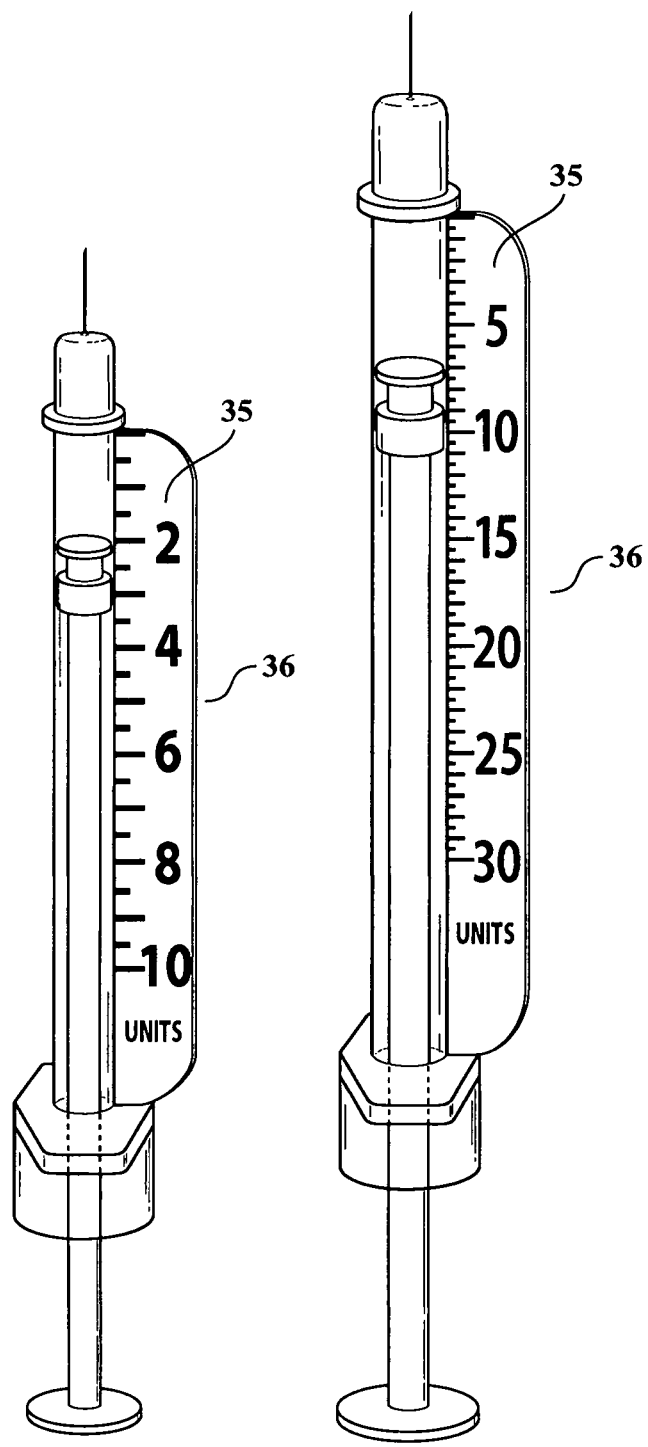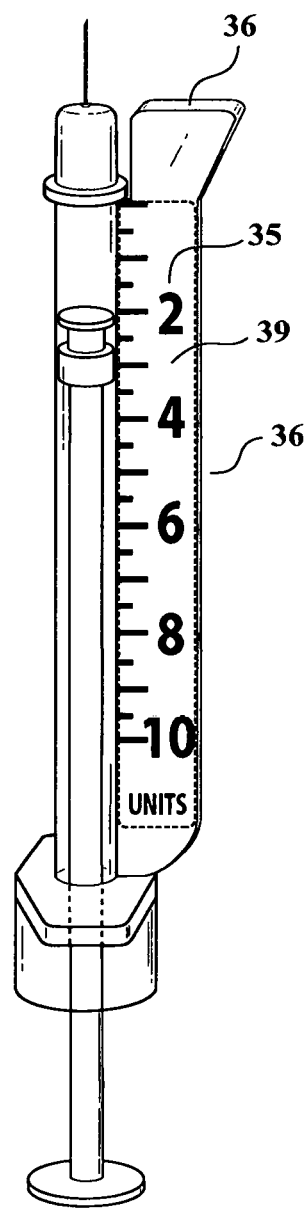
FIG. 5      FIG. 6

SMALL SYRINGE WITH ENHANCED READABILITY

CROSS-REFERENCE TO RELATED APPLICATIONS

This application claims priority under U.S. provisional application Ser. Nos. 62/498,975 filed on Jan. 10, 2017; 62/499,704 filed on Feb. 2, 2017; 62/499,862 filed on Feb. 6, 2017; 62/499,872 filed on Feb. 6, 2017; 62/499,873 filed on Feb. 6, 2017; 62/601,840 filed on Apr. 3, 2017; 62/601,904 filed on Apr. 4, 2017; 62/601,917 filed on Apr. 4, 2017; 62/602,138 filed on Apr. 12, 2017; 62/707,919 filed on Nov. 24, 2017; and, 62/708,564 filed on Dec. 12, 2017.

BACKGROUND

Field of the Invention

This application relates to improved indicia readability on low-volume syringes, particularly syringes for use with insulin.

PRIOR ART

For context of the invention and for orientation and reference in its detailed description, the following is an overview of a conventional one-use insulin syringe.

FIGS. 1A-1E (PRIOR ART): The main body portion of a typical one-use insulin syringe comprises a transparent, cylindrical side wall or barrel 24 with an elongate longitudinal axis. An inner surface of barrel 24 defines a cylindrical lumen or chamber 24b which is coaxial with the wall of barrel 24 and communicates with a short passageway 25b of a barrel hub 25 on a distal end of barrel 24. A proximal end of barrel 24 is open to chamber 24b, and that end connects with a finger flange 26, which connects terminally with a proximal cap mount 28. Flange 26 and mount 28 are bored such that they allow full access to the open end of barrel 24 and chamber 24b. Barrel 24, hub 25, flange 26, and cap mount 28 are typically combined for fabrication from a polymer as a single unit from a common mold, for subsequent connection with two other assemblies: a needle/hub assembly 20/22 and a plunger assembly 30/32, detailed next.

FIGS. 1B-1D (PRIOR ART): The needle hub assembly comprises a hollow metallic needle 20 and a polymeric needle hub 22 for a connection to barrel hub 25. In the fabrication of that assembly, FIGS. 1C and 1D show that needle 20 is embedded in a solid cylinder or needle pillar 23, which is integral to and originates axially within needle hub 22. At assembly, pillar 23 is received by passageway 25b of barrel hub 25 on barrel 24, thereby communicating a lumen of needle 20 with chamber 24b. A wall of needle hub 22 further reinforces the entire connection with a cap-like compression fitting of the assembly onto hub 25 in permanent attachment. When not in use, the needle/hub assembly is covered by a removable cap (not shown).

FIG. 1A (PRIOR ART): Chamber 24b of barrel 24 is inserted with and occupied by a plunger assembly comprising a flexible elastomeric plunger head 32, which is attached to a distal end of a plunger rod 30. Head 32 has two functions: it forms a slideable stack of annular seals for aspirating insulin into and injecting insulin out of barrel 24 through hub 22/needle 20, and its leading annular seal serves as a marker for measuring insulin doses from a dose scale, detailed next.

FIG. 1E (PRIOR ART): Barrel 24—and by extension its associated chamber 24b—has a calibrated or calibratable range A, which originates distally near barrel 24's connection with needle hub 22 and terminates proximally in transition to a non-calibrated aspect B. Aspect B helps to maintain proper axial alignment of plunger rod 30/head 32 in range A. Aspect B of barrel 24 continues proximally to terminate at a junction with finger flange 26. The calibrating lines and numerals for measuring unit doses of insulin with plunger head 32 are presented as a columnar-arranged dose scale 35 on range A of barrel 24's outer wall. Other syringe indicia are also presented on the outer wall of barrel 24. The 30 unit capacity syringe shown is calibrated and marked for whole half units of insulin. Other common capacities for insulin syringes are 50 and 100 units.

FIG. 1E (PRIOR ART): As extremely small and thin tubular structures—or essentially miniaturized syringes—insulin syringes possess minimal surface areas to their outer barrel walls, and sharp curvatures to those surfaces. Consequently, it is challenging to present indicia—most notably a dose scale 35—on barrel 24 without compromised readability or legibility. On barrel 24's curved surface, lines and numerals of dose scale 35 appear horizonal, clipped, and distorted. The smaller the syringe, the greater those limitations. For example, on a conventional 30 unit syringe it is nearly impossible for the user to clearly visualize the dose scale's full field of calibrating lines and numerical markings at once from the same view, thus requiring the barrel to be rotated axially from side to side to gather multiple viewpoints, as shown serially in the photographs in FIG. 1E. Half-unit increments are particularly difficult to present, visualize, and accurately draw to. Other required syringe indicia—textual and glyphic—are also challenging to present and read.

Furthermore, any of a syringe barrel's dose scale 35 markings directly over traveling internal plunger head 32 become obscured; i.e., as shown in FIG. 1E, (black) numerals and lines disappear while they are superimposed on the underlying (black) plunger head 32, effectively blocking visualization of the desired calibrated point—most critically near the end of every dose draw.

In observational studies, readability of an insulin syringe's dose scale is identified as a key problem—and a limiting factor—particularly for diabetics with compromised vision.

Those intrinsic physical limitations for dose scale presentation ultimately restrict how low in capacity and refined in calibration present insulin syringes can be produced; 30 units is currently the smallest syringe available. In pediatrics and small animal veterinary medicine, where doses are smaller and dosing tolerances are intrinsically narrower, a finely calibrated 20, 15, or 10 unit syringe with accurate and readable half-unit scaling would offer superior utility over present offerings.

Various inventions have proposed approaches to improving insulin syringe readability. U.S. Pat. Nos. 4,743,234A, 2,586,581A, 4,178,071A, 6,936,034B2, D790,056S1, 8,636,702B2, 5,062,828A, and publication no. EP0084583A1 disclose means for optical magnification of existing small syringe dose scales.

U.S. Pat. Nos. 4,018,223A, 5,242,405A, 6,120,481A, 9,775,950B2, 9,192,723B2, pre-grant publication nos. US20150306318A1, US20150073354A, US20150231335A1, and publication no. WO2016176523 (A1) disclose means for assistance with dose measurement.

Though the above devices assist in readability of insulin syringes, they involve separate attachments entailing additional operational steps that can further complicate an already intricate and challenging exercise.

Publication Nos. FR2693909A1 and DE4323466A1 disclose a small syringe barrel with an integral flat panel for presentation of a dose scale. However, that panel, by its superimposed/tangential placement directly over the barrel wall, largely obscures the view of the underlying barrel—more critically, its luminal contents. Furthermore, the panel's apposition with the finger flange interferes with the intended function of that part, compromising the syringe's overall ergonomics.

Thus, it would be desirable to pursue more incisive solutions that resolve small syringe readability directly through fundamental design or redesign of the syringe itself, while further advancing its ergonomics and functionality.

BRIEF SUMMARY OF THE INVENTION

The devices of this application render improved dose scale visibility and readability with low-volume injection syringes, particularly syringes for use with insulin. A central element is an elongated, tab-like extension or scale panel which projects radially outward from and courses the syringe barrel's outer wall in a longitudinal and axial manner. The panel provides space for clearer, direct-on, distortion-free presentation of the syringe's dose scale and other indicia, and improved grip and handling dynamics of the syringe during insulin draws and injections. In design, the panel can be extended distally to provide a fore edge or plane of varying possible profiles and dimensions for guidance of injection angle and depth, and injection stability. In design, the panel can be extended proximally to the finger flange for added structural reinforcement of the syringe. The panel can be incorporated with existing syringe designs of various type and utility.

DRAWING FIGURES

[Note: The drawings presented are enlarged views, and are not to scale.]

FIG. 1A (PRIOR ART) is a drawing of a conventional 30 unit insulin syringe with its parts labelled for reference.

FIG. 1B (PRIOR ART) shows an alternative view (rotated 90 degrees axially) of the main syringe body from FIG. 1A, with the needle hub assembly detached.

FIG. 1C (PRIOR ART) is an enlarged view of the distal end of the conventional syringe from FIGS. 1A and 1B, which is marked for a sectional view through its longitudinal axis in FIG. 1D.

FIG. 1D (PRIOR ART) is an axial sectional view of the syringe view of FIG. 1C.

FIG. 5 shows a frontal view of the fifth syringe (on the left) which is configured in a 10 insulin unit capacity, in a direct scaled comparison with the 30 unit capacity second syringe on the right (and also shown in FIG. 3).

FIG. 6 shows a frontal view of the sixth syringe, which is configured in a 10 unit capacity, has a distally extended scale panel, and has its dose scale presented on an adhesive label (dotted line).

Figure 1E:
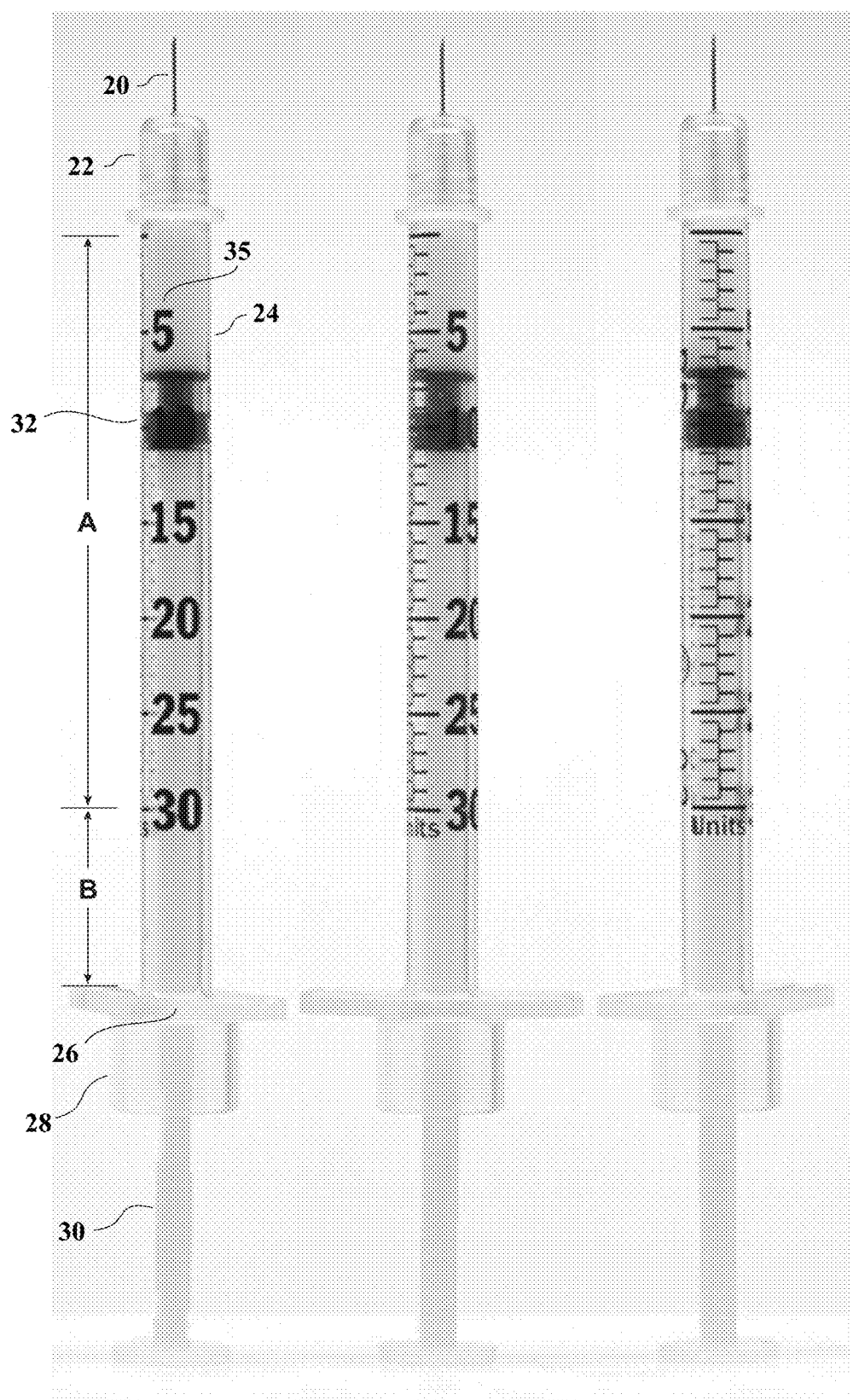
FIG. 1E (PRIOR ART) is a composite photograph of a conventional 30 unit insulin syringe which is shown rotated axially to three different positions to view its dose scale.

| REFERENCE NUMERALS | | | |
|---|---|---|---|
| 20 | needle | 32 | plunger head |
| 22 | needle hub | 35 | dose scale |
| 23 | needle pillar | 36 | scale panel |
| 24 | barrel | 38 | nozzle tip |
| 24b | chamber of barrel | 39 | scale label |
| 25 | barrel hub | 40 | needle shielding mechanism |
| 25b | passageway of barrel hub | A | calibrated/calibratable range of barrel |
| 26 | finger flange | B | non-calibrated aspect of barrel |
| 28 | proximal cap mount | C | spacing between scale panel and needle hub |
| 30 | plunger rod | | |

DETAILED DESCRIPTION OF THE INVENTION

First Syringe: FIGS. 2A-2D

Figure 2A:
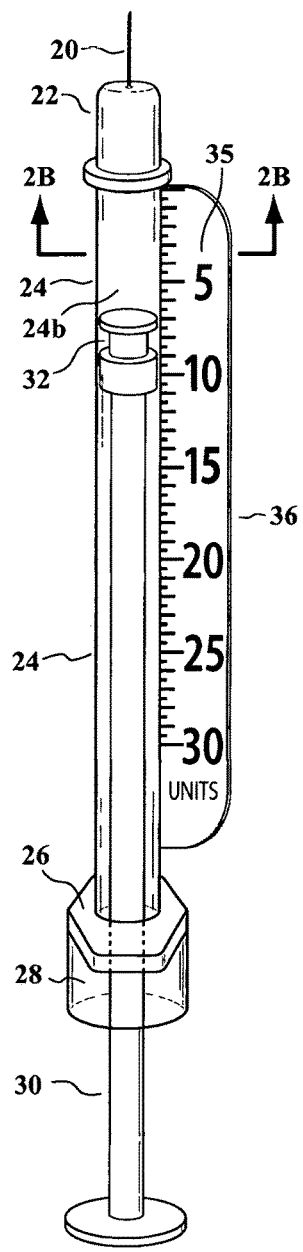
FIG. 2A shows a frontal view of the first syringe, which is marked for a sectional view in FIG. 2B.

FIG. 2A shows a frontal view of a first syringe which embodies the same general structure, scale and capacity, numbered parts, and part orientations of the conventional 30 unit insulin syringe as described above under Background/Prior Art and illustrated in FIGS. 1A-1E, and adds a scale panel 36.

Scale Panel 36: FIGS. 2A-2D

Figure 2B:
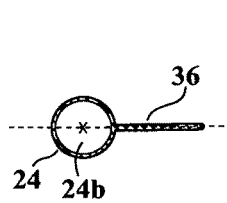
FIG. 2B shows a sectional view of the first syringe in FIG. 2A to show how the scale panel aligns perpendicularly with the syringe barrel wall, and how the scale panel's main plane of symmetry (dotted line) includes the syringe barrel chamber's longitudinal axis (X).

Scale panel 36 comprises an elongate, tab-like, planar projection from an outer surface of a wall of a barrel 24, which is in alignment with a longitudinal axis of barrel 24 and its associated barrel chamber 24b. A sectional view in FIG. 2B shows panel 36 with its two main surfaces or faces—front and rear—as an outward radial projection from barrel 24's outer wall and longitudinal axis. More specifically, FIGS. 2B and 2D show panel 36 as perpendicular to the curved outer wall of barrel 24, such that panel 36's main plane of symmetry (dashed line) includes the longitudinal axis (X) of barrel 24/barrel chamber 24b. Accordingly, the two main faces of panel 36 are near-perpendicular to the outer wall of barrel 24, for indicia-displaying advantages described below.

As it courses the outer wall of barrel 24, panel 36's length incorporates a calibratable/calibrated aspect or range A of barrel 24 and chamber 24b from their origins near needle hub 22 (with an added margin proximally of a non-calibrated aspect B of barrel 24 to provide for an item of indicium, "UNITS")

Figure 2C:
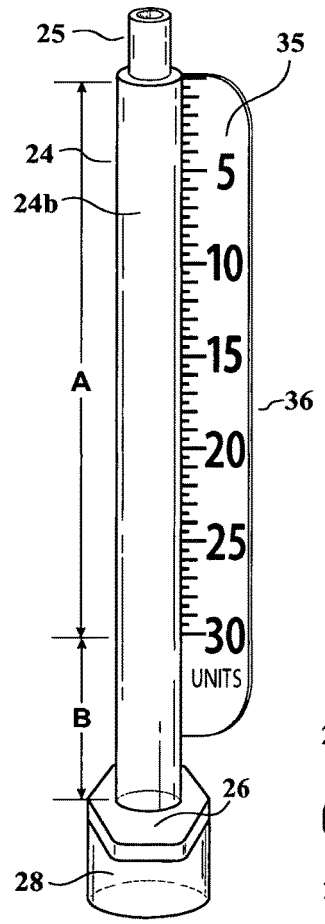
FIG. 2C shows a frontal view of the first syringe's main body, sans needle/needle hub and plunger assembly.
Figure 2D:
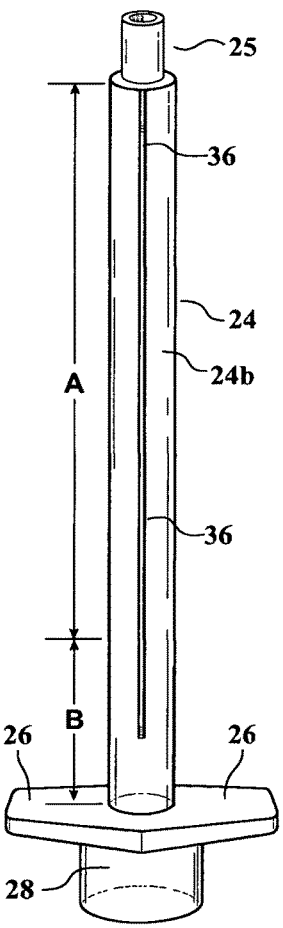
FIG. 2D shows the syringe body of FIG. 2C rotated axially one quarter of a turn to the right.

For optimal syringe ergonomics in this first version and other versions infra where a finger flange 26 provided, panel 36 is shown positioned on barrel 24 such that its (extended) main plane is perpendicular to, and bisecting of, an upper longitudinal plane of flange 26 (FIGS. 2A, 2C, 2D). Other angles between barrel 24, panel 36, and flange 26 are possible.

On a front surface of scale panel 36 an imprinted dose scale 35 is shown. In this example, scale 35 provides for nearest half-unit increments of insulin measurement in its 30 unit calibrated range A on barrel 24. At dose measurement a lateral edge of plunger head 32's leading annular seal is aligned with a lateral edge of a desired line/insulin unit quantity of scale 35 on panel 36 (for example, in FIG. 2A seven units is the dose quantity selected).

Scale panel 36 with its outward and perpendicular positioning on barrel 24 offers a plurality of advantages:

- On the flat surface of panel 36, dose scales can be presented in a direct, face-on, distortion-free manner, and be visualized clearly and totally in a single view without need for rotation of barrel 24 side to side (as with the conventional syringe in FIG. 1E).
- Panel 36 allows for a potential plurality of advanced dose scale configurations. For example, dose scale 35 of syringe versions shown infra moves all dose scale markings from barrel 24 onto panel 36, leaving a clear and unimpeded front view of barrel 24's contents and essential visual targets—insulin/air and the plunger assembly within. As such, unlike with conventional syringes (FIG. 1E), plunger head 32 does not obscure overlying dose scale lines and numerals during its travels within barrel 24—particularly near the end of each dose draw. Furthermore, using that specific dose scale 35 layout as an example, panel 36's lateral and radial positioning on barrel 24 allows dose scale lines of scale 35 on panel 36 to be aligned directly edge-to-edge with the leading annular seal of plunger head 32. The effect of that is a more focalized and precise means for dose measurement over conventional layouts with on-barrel presentation of dose scale lines superimposed over plunger head 32, or modified syringes bearing dose scales on panels positioned tangentially on barrel 24.
- Panel 36 provides more space for bolder, more legible printed indicia markings (or embossed markings, raised or relief). Panel 36 can also provide writable spaces for additional patient specifics. Any additional indicia markings can be applied to a rear surface of barrel 24 and/or to a rear surface of dose scale panel 36. For the syringe versions shown herein, assume that other required indicia—textual and glyphic labeling excluding dose scale 35—would be placed on the rear face of barrel 24 and/or the rear surface of panel 36.]
- It is also possible to present indicia—notably dose scale 35—on panel 36 with high contrast, high resolution printed adhesive labelling, vs. current surface printing methods with their resolution limitations. FIG. 6 shows a sixth syringe with an adhesive scale label 39 (dotted line) applied to scale panel 36. For the panel's rear surface, the label's backing would then provide a bright background for panel-printed indicia or writable space, if elected.
- Dose scale panel 36 adds body and grip to the thin syringe barrel 24. Braced between the fingers, panel 36 also lends axial stability to the syringe's handling dynamics, reducing both roll and pitch of barrel 24 at all attitudes, and ultimately reducing aberrant needle movement/pain at injection.

Thus, a syringe barrel with scale panel 36 possesses three distinct surfaces upon which indicia can be presented: two panel 36 surfaces (front and rear), and the surface of barrel 24. The first syringe shows just one of many possible configurations for any dose scale or other indicia display that may be desired—including on and/or off barrel 24 presentation.

Description—Alternative Embodiments

Figure 3:
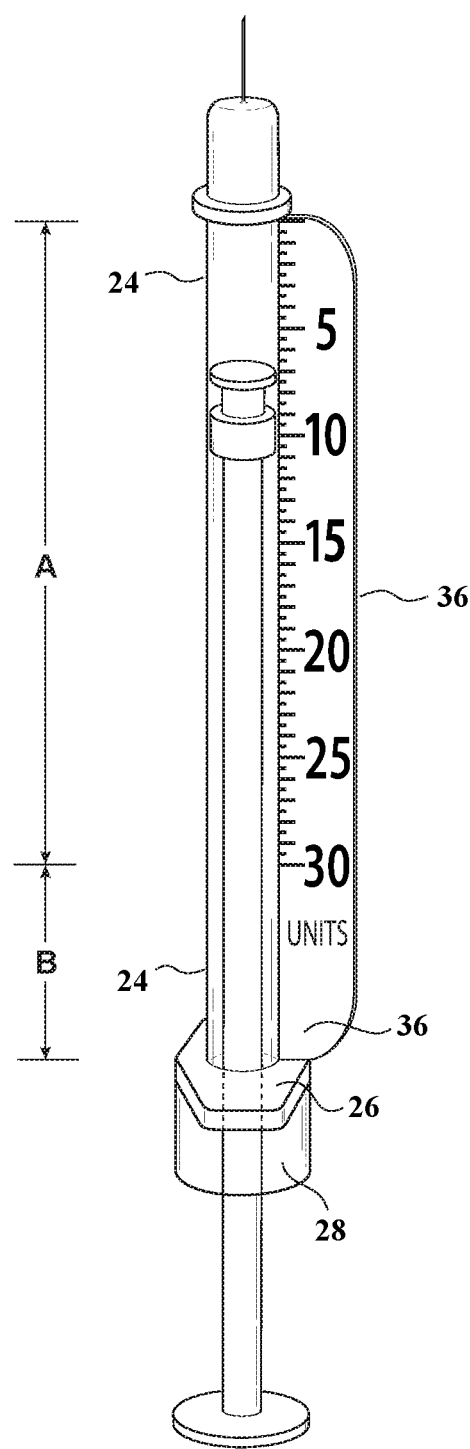
FIG. 3 shows a frontal view of the second syringe.

FIG. 3 shows a second syringe which is identical to the first syringe above, with the exception that scale panel 36 has been extended proximally—beyond calibrated range A of barrel 24 to include non-calibrated aspect B of barrel 24—to terminate with an integral connection with finger flange 26. As such, barrel 24, panel 36, flange 26, and proximal cap mount 28 are preferably fabricated as a unitized piece from a common mold, thus adding structural strength to the syringe body and further enhancing its overall grippability and axial stability in use. That collateral reinforcement may also ultimately allow barrel 24 to be molded and fabricated with thinner walls, thereby further increasing barrel 24's transparency and the visibility of its contents.

Figures 4A, 4B, 4C:
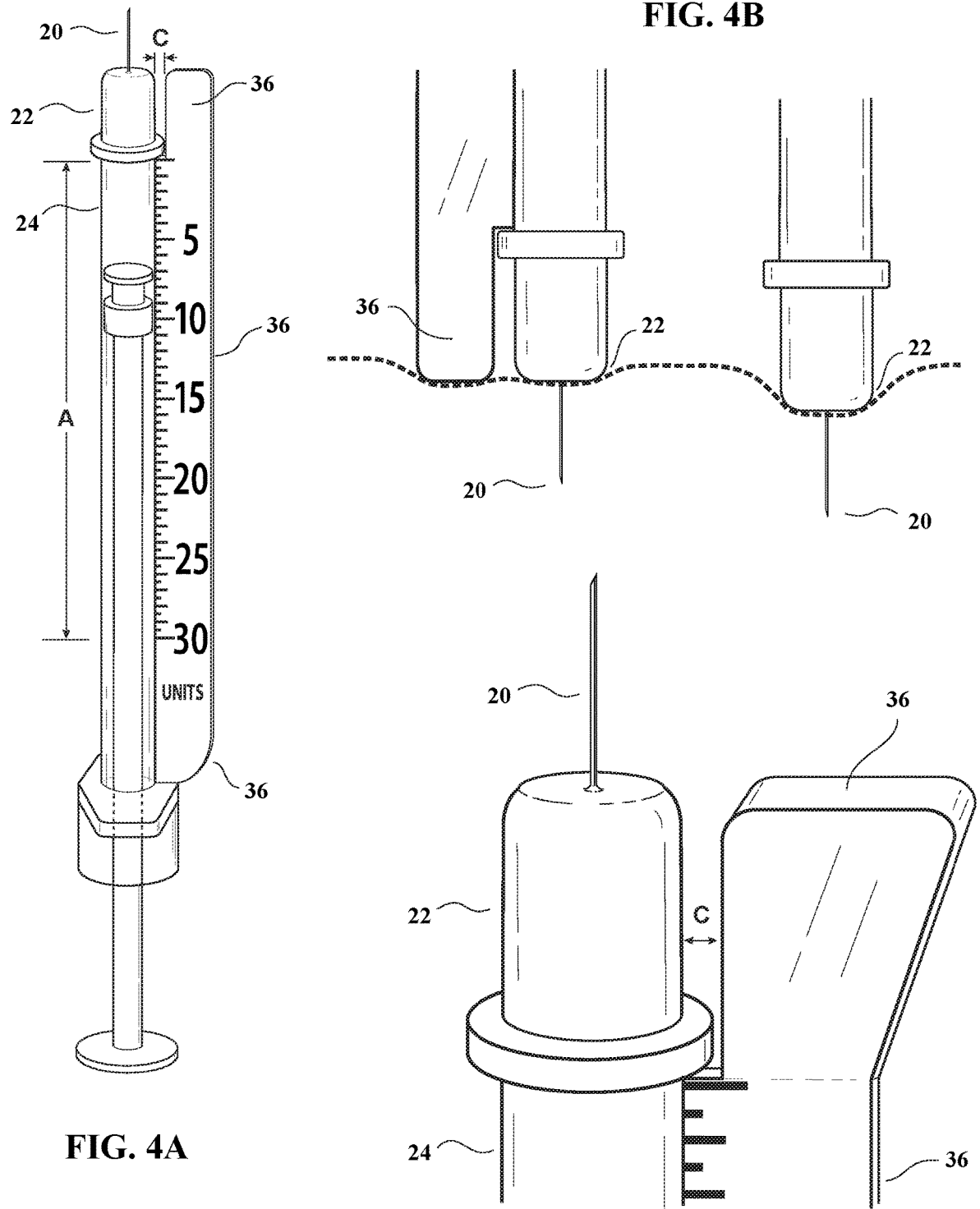
FIG. 4A shows a frontal view of the third syringe.
FIG. 4B shows injection dynamics at the skin surface (dotted line) of the third syringe (left side) in comparison with a conventional insulin syringe (right side).
FIG. 4C is an enlarged frontal view of the fourth syringe's distal aspect to show an expanded distal edge of the distally extended scale panel.

FIG. 4A shows a third syringe which is identical to the second syringe in FIG. 3, with the exception that scale panel 36 has been extended distally—beyond calibrated range A of barrel 24—to flank needle hub 22 and terminate distally as a straight edge at a desired alignment (approximately level) with the distal end or face of hub 22. A spacing C is provided between hub 22 and an inside edge of distally extended panel 36, such that a regular needle/hub cap can be attached in an existing manner.

This distally extended scale panel 36 adds utility to the syringe:

- The distal edge of distally extended panel 36 provides the patient with a straightedge visual guide in the approach for a preferred, straight-in 90-degree needle axis-to-skin plane angle of injection. The 90 degree injection angle is requisite with the newer shorter needle lengths on insulin syringes.
- The diagram in FIG. 4B compares the third syringe (left) with a conventional syringe (right) at injection through the skin (dotted line). When planted flatly against the skin, the distal edge or narrow distal plane of third syringe's distally extended scale panel 36 functions as a visual guide and a physical limitation or stop to aberrant/excess advancement of needle 20/hub 22 deeper into the tissue at needle insertion and injection—in comparison with the conventional syringe's more focalized hub pressure and its variable "dimpling" and depth effects. The net effect is a more predictable and consistent injection depth—a critical factor with insulin use where needle lengths are designed and appropriated to task by nearest 1 mm tolerances.
- The distal edge of distally extended scale panel 36 also helps to brace and stabilize against aberrant sideways axial and fore/aft movements of needle 20/needle hub 22 after insertion and during injection, reducing tissue trauma and injection pain. The edge also promotes a more square and stable plant against the stopper of an insulin vial at dose draws.

The above improvements in injection technique may open the possibility for even shorter needle lengths—e.g., 4 mm or 5 mm vs. the current 6 mm minimum for insulin syringes—for less painful injections.

The third syringe above and in FIGS. 4A and 4B shows a rudimentary example of a distally extended scale panel 36 as an injection guide. For a greater surface area to plant against the skin surface—and thus greater stabilization effects described above—a distally extended scale panel 36 could be further widened and/or broadened in its distal-edge or plane. A fourth syringe in FIG. 4C shows a distally-extended scale 36 which has been expanded to render a deeper and wider, more planar distal edge. That same configuration of FIG. 4C is scaled down and adapted to a 10 unit syringe in a sixth syringe shown in FIG. 6. Many different shapes and expansions to that extended area of panel 36 are possible, and can include texturizations for added skin contact dynamics. Alternatively, a rudimentary distally extended scale panel 36—e.g., as shown on the third syringe in FIG. 4A—could function as a mount for attachments with more complex shapes, skin contact dynamics, and injection-modifying effects.

In design, a syringe's preferred injection depth can be preset through relative positioning of the distal edge/plane of distally extended scale panel 36 with the distal plane or face of needle hub 22—e.g., leading to, level with, or countersunk/recessed to.

Description—Other Modifications

Above syringes are shown scaled and calibrated for 30 unit insulin capacities and nearest half-unit dose measurements. Other capacities (e.g., standard 100 units, 50 units, etc.) and calibrations (e.g., nearest unit, half unit, or quarter unit) are possible. FIG. 5 shows a fifth syringe (on the left) with a 10 unit insulin capacity, which is a scaled-down version of the 30 unit capacity second syringe (above and in FIG. 3), shown side by side for comparison. FIG. 6 shows the sixth syringe, which is a scaled down, 10 unit version of the fourth syringe from FIG. 4C.

Figure 8:
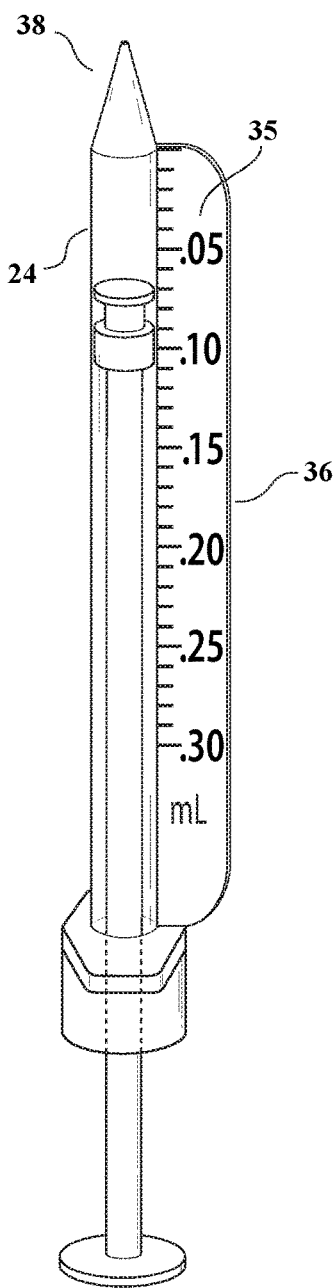
FIG. 8 shows a frontal view of the eighth syringe, which has a dose scale calibrated for mL, and has been fitted with a nozzle, vs. an injection needle.

Volume capacities and calibration metrics (e.g., cc, mL, mg equivalents, and fractions thereof) for other injection utilities and other dosing routes (e.g., oral or topical) are possible. FIG. 8 shows an eighth syringe in where scale panel 36 displays dose scale 35 in mL fractions, and barrel 24 is fitted with an nozzle tip 38—vs an injection needle.

The flat surfaces of scale panel 36 allow for a plurality of potential dose scale configurations, in combination with markings on barrel 24—or in place of, as shown in the above versions. Panel 36 can be provided in either a left or a right (shown herein) orientation on barrel 24. Both front and rear surfaces of panel 36 are utilizable for indicia presentations. Additional syringe information can be placed on the rear surface of panel 36 or the rear aspect of barrel 24 (thereby allowing the front face of barrel 24 to remain completely marking-free for optimal visibility of its luminal contents). Designated areas of panel 36 for writable spaces can be finely etched or texturized to further enhance that feature. Similarly, larger areas or entire surfaces of panel 36 may be etched for greater opacity or a "frosted" appearance, and thus a higher contrast background for indicia. Per above, some or all of indicia—notably dose scale 35—can be presented on panel 36 via high contrast, high resolution adhesive labelling.

Scale panel 36 improves the user's grip of the syringe. At dose draw and injection, panel 36 functions as a symmetrical and balanced fin-like brace between the fingers, fixing barrel 24 from rolling on its longitudinal axis or pitching on its transverse axis—for steadier dose draws and injections. In a mold design, the short, non-calibrated aft section of barrel 24 and/or panel 36—just proximal to finger flange 26—can be built up in profile and/or texturized to further bolster this effect, and thus possibly preclude the need for a conventional finger flange 36. Similarly, the upper surface of finger flange 26 and the proximal end of plunger rod 30 can be texturized for added grip dynamics.

Scale panel 36 can be contoured in its general width, length, shape, or thickness for a desired utility and design. Other shapes may include elongate curves or ovoid forms. The rounded rectangular-shaped panel 36 shown for versions herein is but one example.

Figure 7:
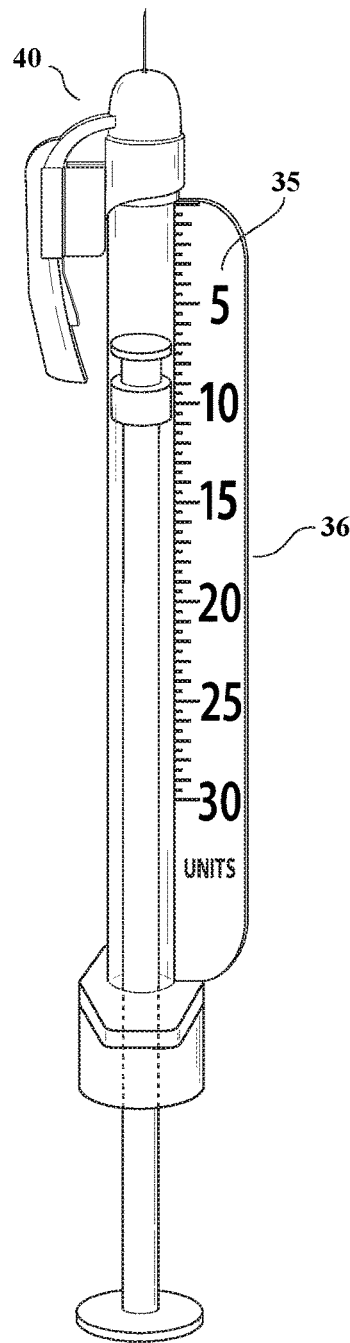
FIG. 7 shows a frontal view of the seventh syringe, which is a modification of a PRIOR ART insulin syringe with a needle shielding mechanism.

Above design principles are readily adaptable to most conventional syringes, other modified insulin injection syringes, syringes with other types of plunger heads—including O-ring types, and low-volume syringes in other metrics and for other applications—e.g., medical, dental, veterinary, lab, research etc. FIG. 7 shows a (PRIOR ART) insulin syringe with a (PRIOR ART) accessory sliding needle shielding mechanism 40, which renders a seventh syringe version by adding scale panel 36 with an off-barrel dose scale 35. FIG. 8 shows the eighth syringe version with scale panel 36 and a dose scale 35 which has been calibrated for nearest 0.01 mL dosing, and to which a nozzle tip 38 has been attached—vs. an injection needle. This version may be used for administering oral or topical medications, or dispensing other types of fluids in other utilities, such as industrial, consumer goods/home use etc.

Figure 9:
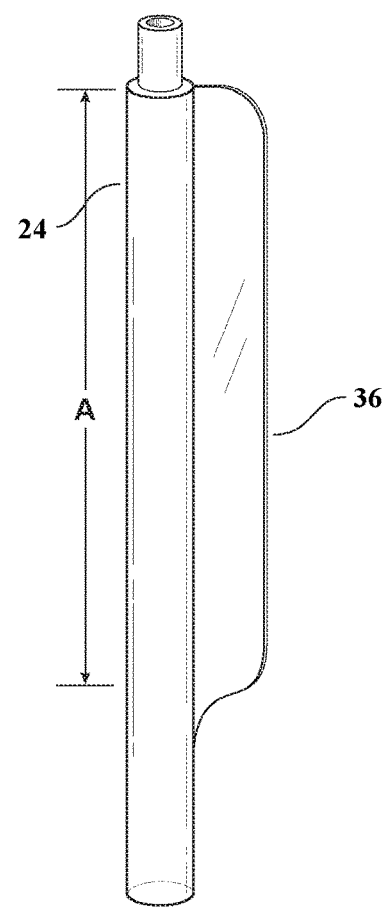
FIG. 9 shows a frontal view of the main body of the ninth syringe, which is absent a finger flange and a rear cap mount.

The syringe versions above have a finger flange 26 and proximal cap mount 28, and most are shown configured as described originally for the second version above—with scale panel 36 extending to and connecting with flange 26. Alternatively, a panel 36 could be incorporated with a barrel 24 sans an integral finger flange 26 or a rear cap mount 28; FIG. 9 shows a ninth syringe with such a configuration, with panel 36 accommodating a calibratable range A of barrel 24.

In summary, the most rudimentary iteration shown as the first embodiment above can be built upon with modifications from other versions shown, alone or in combination, e.g.,: distal extension of scale panel 36 for an injection guide; further expansion of any distal extension of panel 36 for greater area of skin contact; and, proximal extension of panel 36 to finger flange 26 for structural reinforcement of barrel 24, Description—Operation Syringe versions shown herein are operated in essentially the same general manner as conventional insulin syringes, utilizing the additional features and functions as described.

Description—Fabrication

Components of the above syringes are preferably fabricated from materials suitable for utility with fluids of intended use. These materials may include various polymers currently in use for conventional insulin syringes (e.g., polypropylenes, polyethylenes, nylon, PFTE or Teflon®-type polymers or additives, elastomeric formulations, silicones, etc.).

Existing syringe fabrication methods—e.g., extrusion, injection, or blow molding—could be used to form barrel 24, scale panel 36, finger flange 26, and proximal cap mount 28, preferably as a single piece from a common mold. Any extension or expansion of scale panel 36 can be accomplished within that common mold. Alternatively, panel 36 could be fabricated as a separate part for subsequent attachment to a desired aspect of barrel 24. Additional surface treatments of panel 36 for any desired texture or opacification can be executed by existing methods. As necessary, any separate parts or assemblies could be attached by existing methods (e.g., ultrasonic welding, adhesives, compression fitting, etc.).

Volumetric lines, numbers, and other figures on barrel 24 and/or panel 36 surface can be rendered by existing application and printing methods. Embossed markings, raised or relief, are another possibility. The above versions allow possible provision of some or all syringe indicia in high-resolution, high contrast adhesive labels for application to scale panel 36, vs. printing directly onto the syringe. That would be particularly advantageous for display of dose scale 35.

By existing methods needle 20 and needle hub 22 can be fabricated as a single unit for attachment onto barrel hub 25 of barrel 24 with compression fitting/ultrasonic welding/adhesive. Plunger rod 30 and plunger head 32 can be fabricated by their respective existing methods, then assembled for insertion to barrel 24. Associated needle caps and rear caps can be fabricated by existing methods.

CONCLUSIONS, RAMIFICATIONS, AND SCOPE

Accordingly, the reader will see that above embodiments offer significant advantages over conventional one-use insulin syringes and other low-volume syringe designs. They are more equipped for the 0.005 mL tolerance demands of half-unit insulin dosing. They also promote more accurate and stable injection technique.

Scale panel 36 eliminates the crowding and parallax distortion of dose scales and other indicia on the curved wall of barrel 24, instead presenting those markings and figures on a flat plane for more effortless, direct-on viewing. Both front and rear surfaces of panel 36 provide generous surface area for bolder scale lines, numerals, text, and glyphs. Accordingly, as described and illustrated for the embodiments herein, it is possible to move all dose scale markings and text, and glyphs off of barrel 24, rendering a full and unobstructed view of insulin and plunger head 32 at dose draws and injections. It is also possible to present indicia on scale panel 36 on a separate, high-resolution printed adhesive label (FIG. 6). Writable space on panel 36 is another option—on both front and rear surfaces.

Scale panel 36 can be further fortified and fully extended to finger flange 26 to function further as a supporting framework around barrel 24, thereby allowing possible reduction of barrel 24's wall thickness, and further improve visibility of its luminal contents. Panel 36 also promotes a more secure grip, for rotational and pitch stability of the syringe's longitudinal axis at all positions during use, for more stable draws and injections.

Syringe versions with scale panel 36 extended fore (FIGS. 4A, 4C, 6) enable improved injection dynamics—alignment, depth-control, and axial stabilization—for a more accurate, consistent, and comfortable injection effect.

The collective effect is an insulin syringe with improved readability, ergonomics, and injection dynamics.

The design breaks barriers to production of ultra-low capacity insulin syringes—e.g., 10, 15, 20 units—with more precise half-unit (possibly ¼ unit) calibrations for critical applications, e.g., pediatrics and small animal medicine. A collateral benefit of this design with extremely small syringes is that their dose scales intrinsically present relatively extended and less crowded—an effect which is further potentiated by scale panel 36 with its clear, direct-on presentation. FIGS. 5 and 6 show 10 unit syringes configured with scale panels and highly readable dose scales.

Above design principles are readily adaptable to most conventional syringes—with or without finger flange 26 and/or rear cap mount 28 (FIG. 9), to other existing modified insulin syringes (FIG. 7), and to many other types of low-volume injection syringes within in a broad range of utilities: medical, dental, veterinary, lab/research, etc.

The design can also be adapted to non-needled syringes (FIG. 8) for other types of refined dispensing or measuring utilities, e.g., oral or topical medications, animal husbandry, horticulture, aquaculture, industrial, consumer goods, home use, etc.

Thus the scope of the embodiments should be determined by the ensuing claim and its legal equivalents, rather than by the examples given.

What is claimed is:

1. A syringe barrel comprising:
    an elongate body portion having a side wall defining a cylindrical chamber with a longitudinal axis, said body portion having an open proximal end and a distal end having a passageway therethrough in communication with said chamber;
    said wall having a generally oblongular projection in longitudinal alignment with said wall and said body portion, said projection extending laterally outwardly and away from said wall in a single general direction, said projection extending longitudinally to or beyond a distal limit of said chamber;
    said projection having a front major face and a rear major face, each of said faces being contiguous along a respective continuous inner longitudinal edge with an outer surface of said wall; and,
    one or each of said faces bearing immediate presentation of markings of a graduated scale, or other indicia, or both.

* * * * *